US00PP26007P3

(12) United States Plant Patent

Klemm et al.

(10) Patent No.: US PP26,007 P3

(45) Date of Patent: Oct. 20, 2015

(54) POINSETTIA PLANT NAMED 'NPCW14205'

(50) Latin Name: *Euphorbia pulcherrima*
Varietal Denomination: NPCW14205

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 142 days.

(21) Appl. No.: 13/999,090

(22) Filed: Jan. 9, 2014

(65) Prior Publication Data

US 2015/0195984 P1 Jul. 9, 2015

(51) Int. Cl.
*A01H 5/00* (2006.01)

(52) U.S. Cl.
USPC ..... Plt./307

(58) Field of Classification Search
USPC ..... Plt./307
See application file for complete search history.

*Primary Examiner* — Annette Para

(74) *Attorney, Agent, or Firm* — James M. Weatherly; Barbara Campbell; Cochran Freund & Young, LLC

(57) ABSTRACT

A new poinsettia plant particularly distinguished by having dark red, elongated bracts, dark green leaves, very high vigor, nine week response time, moderate cyathia quantity, and strong stems, is disclosed.

1 Drawing Sheet

Genus and species: *Euphorbia pulcherrima.*
Variety denomination: 'NPCW14205'.

BACKGROUND OF THE NEW PLANT

The present invention comprises a new and distinct variety of poinsettia, botanically known as *Euphorbia pulcherrima* and hereinafter referred to by the variety name 'NPCW14205'. 'NPCW14205' is a selection from a cross-pollination of the proprietary female *Euphorbia* line 'EP-2005-0103' (unpatented) and the proprietary male *Euphorbia* line 'EP-2005-0028' (unpatented).

In November/December of 2007 the proprietary female *Euphorbia* line 'EP-2005-0103' and the proprietary male *Euphorbia* line 'EP-2005-0028' were cross pollinated in Nairobi, Kenya and seeds were obtained. The seeds were sown and plants were grown for evaluation. A plant line was selected in November 2008 in Stuttgart, Germany and named 'NPCW14205'. In May 2009, 'NPCW14205' was first vegetatively propagated by vegetative cuttings. 'NPCW14205' was found to reproduce true to type in successive generations of asexual propagation via apical cuttings in Stuttgart, Germany.

SUMMARY

The following are the most outstanding and distinguishing characteristics of this new variety when grown under normal horticultural practices in Stuttgart, Germany.

1. Dark red, elongated bracts;
2. Dark green leaves;
3. Very high vigor;
4. Nine week response time;
5. Moderate cyathia quantity; and
6. Strong stems.

DESCRIPTION OF THE PHOTOGRAPH

This new poinsettia plant is illustrated by the accompanying photograph which shows an overall view of the plant. The photograph is of a plant approximately four months old grown indoors Stuttgart, Germany in December 2010. The colors shown are as true as can be reasonably obtained by conventional photographic procedures.

DESCRIPTION OF THE NEW VARIETY

The following detailed descriptions set forth the distinctive characteristics of 'NPCW14205'. The data which define these characteristics were collected from asexual reproductions carried out in Stuttgart, Germany. Data was collected on four month old plants grown indoors in Stuttgart, Germany under greenhouse conditions in the fall of 2013. Color references are to The R.H.S. Colour Chart of The Royal Horticultural Society of London (R.H.S.), 5$^{th}$ edition (2007).

Classification:
- *Family.*—Euphorbiaceae.
- *Species.*—*Euphorbia puicherrima.*
- *Common name.*—Poinsettia.
- *Variety.*—'NPCW14205'.

Parentage:
- *Male.*—Proprietary *Euphorbia* line 'EP-2005-0028'.
- *Female.*—Proprietary *Euphorbia* line 'EP-2005-0103'.

Growth:
- *Time to produce a rooted cutting.*—4 weeks.
- *Blooming habit.*—Intermittent.
- *Flowering response time.*—Approximately 63 days.
- *Keeping quality.*—Very good.

Plant description:
- *Form.*—Triangular.
- *Growth habit.*—Upright.
- *Height.*—30.0 cm to 32.0 cm.
- *Width.*—35.0 cm to 38.0 cm.
- *Number of branches.*—5 to 6.
- *Average number of inflorescences per plant.*—5.5.

Propagation:

*Type cuttings*.—Apical cuttings.

*Time to produce a rooted cutting*.—4 weeks.

Stems:

*Color*.—RHS 143A, on parts of the stem stripes and regions of RHS 181A.

*Length*.—24.0 cm to 26.0 cm.

*Internode length*.—1.5 cm to 3.5 cm.

*Diameter*.—0.5 cm to 0.8 cm.

Leaves:

*Quantity*.—6 to 7 per lateral branch.

*Arrangement*.—Alternate.

*Shape*.—Ovate.

*Apex*.—Acute.

*Base*.—Obtuse.

*Margin*.—Serrate.

*Lobes*.—Lobation characteristics: Moderately deep. Texture (both surfaces): Smooth. Vein color: Upper surface: Transparent. Lower surface: RHS 139D, middle vein and other veins towards the leaf base changing into RHS 181.

*Variegation*.—Absent.

*Size*.—Length: 4.0 cm to 10.0 cm. Width: 3.0 cm to 8.0 cm.

*Color*.—Mature foliage: Upper surface: RHS 139A. Lower surface: RHS 139D. Immature foliage: Upper surface: RHS 141A. Lower surface: RHS 139B.

*Leaf petiole*.—Length: 3.0 cm to 6.0 cm. Diameter: 0.2 cm to 0.3 cm. Color: Upper surface: RHS 59A. Lower surface: RHS 181B.

Inflorescence:

*Lastingness of inflorescence on the plant*.—4 weeks.

*Diameter*.—18.0 cm to 22.0 cm.

*Height*.—3.0 to 4.0.

*Fragrance*.—Absent.

Bracts:

*Number of bracts per inflorescence*.—8 to 10.

*Shape*.—Ovate.

*Apex*.—Acute.

*Base*.—Obtuse.

*Margin*.—Slightly serrate.

*Size*.—Length:7.0 cm to 11.0 cm. Width: 4.0 cm to 6.0 cm.

*Texture*.—Upper surface: Smooth. Lower surface: Smooth.

*Vein color*.—Upper surface: RHS 59A. Lower surface: RHS 181B.

*Bract color*.—Upper surface: RHS 46B. Lower surface: RHS 47B.

*Bract petiole*.—Length: 0.5 cm to 2.0 cm. Diameter: 0.2 cm to 0.3 cm. Color: Upper surface: RHS 59A. Lower surface: RHS 181B.

Cyme:

*Diameter*.—1.0 cm to 2.0 cm.

*Cyathia number*.—4 to 6 per inflorescence.

*Cyathium*.—Shape: Ovate. Diameter: 0.2 cm to 0.5 cm. Length: 0.3 cm to 0.7 cm. Color: RHS 143C.

*Peduncle*.—Color: RHS 142B. Length: 0.2 cm to 0.6 cm.

*Nectar cups*.—Number: 1 per cyathium. Diameter: 0.1 cm. Size: 0.3 cm to 0.4 cm. Color: RHS 14C.

Reproductive organs:

*Stamens*.—Quantity: 5 to 8 per cyathium. Shape: Ovate.

*Filament*.—Length: 0.25 cm. Color: RHS 46A.

*Pollen*.—Quantity: Sparse. Color: RHS 12A.

*Fruit and seed set*.—Low fruit and seed set.

COMPARISON WITH PARENTAL LINES AND KNOWN VARIETY

'NPCW14205' is a distinct variety of poinsettia having dark red bracts. 'NPCW14205' is distinguished from its parents as described in Table 1:

TABLE 1

Comparison with Parental Lines

| Trait | Variety 'NPCW14205' | Female parent 'EP-2005-0103' | Male Parent 'EP-2005-0028' |
|---|---|---|---|
| Bract color | Dark red | Darker than 'NPCW14205' | Lighter red than 'NPCW14205' |
| Leaf color | Dark green | Dark green | Light green |
| Response-time | 9 weeks | 8.5 weeks | 8 weeks |

'NPCW14205' is most similar to the commercial poinsettia plant named 'Prestige Red' (patent status unknown). Differences between the two varieties are described in Table 2:

TABLE 2

Comparison with Similar Variety

| Trait | Variety 'NPCW14205' | Commercial line 'Prestige Red' |
|---|---|---|
| Cyathia-quantity | Moderate | Higher quantity than 'NPCW14205' |
| Vigor | Very high vigor | Medium to high vigor |
| Stem-strength | Strong | Very strong |
| Bract-shape | More elongated than 'Prestige Red' | Less elongated than 'NPCW14205' |

We claim:

1. A new and distinct variety of poinsettia plant named 'NPCW14205' as shown and described herein.

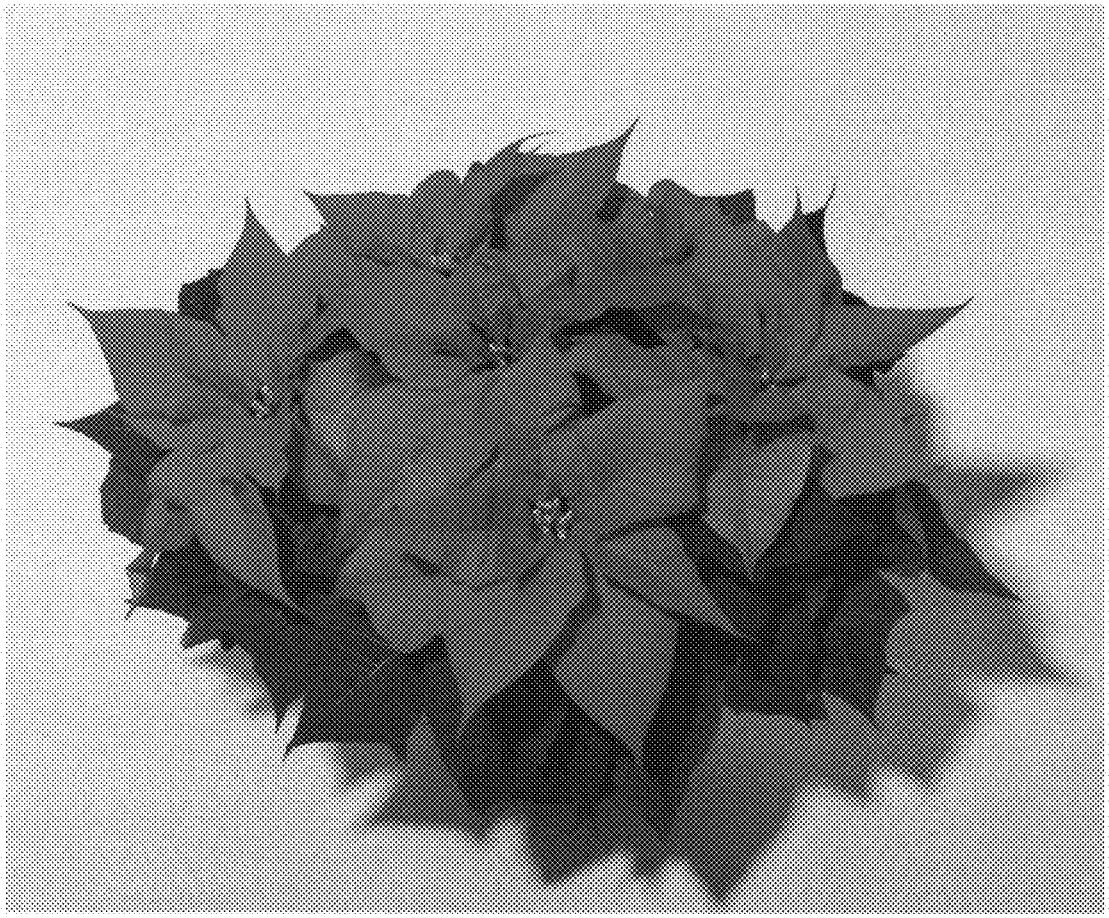

* * * * *